United States Patent [19]

Jones

[11] Patent Number: 4,982,843
[45] Date of Patent: Jan. 8, 1991

[54] SHARPS DISPOSAL UNIT

[76] Inventor: Hedwig E. Jones, 3519 Gemini Ct., Concord, Calif. 94519

[21] Appl. No.: 491,200

[22] Filed: Mar. 2, 1990

[51] Int. Cl.$^5$ .......................... B65B 43/20; B65B 85/24
[52] U.S. Cl. ..................................... 206/366; 206/807; 220/346; 220/908
[58] Field of Search ............... 220/345, 346, 347, 1 T; 206/363, 807, 365, 366, 367

[56] References Cited

U.S. PATENT DOCUMENTS

| | | | |
|---|---|---|---|
| 85,647 | 1/1869 | Dolan | 220/346 X |
| 1,325,349 | 12/1919 | Burgess | 220/346 X |
| 2,941,691 | 6/1960 | Weinberg | 220/346 |
| 3,630,344 | 12/1971 | Bergh et al. | 220/345 X |
| 4,303,178 | 12/1981 | Ford, Jr. | 220/345 |
| 4,340,140 | 7/1982 | Wilcox et al. | 220/346 X |
| 4,688,023 | 8/1987 | McGill et al. | 220/346 X |
| 4,898,276 | 2/1990 | Georgakis | 220/347 X |

*Primary Examiner*—Paul T. Sewell
*Assistant Examiner*—Jacob K. Ackun, Jr.

[57] ABSTRACT

A device that forms a single-use disposal unit for sharp objects like needles and syringes, that is safe and easy to use and contains the spread of infection. It can double as a supply unit and is especially valuable for in-home care. It consists of a plastic box with an unattached, flat lid. The lid can slide into the box in such a way as to lock the box permanently.

2 Claims, 1 Drawing Sheet

U.S. Patent
Jan. 8, 1991
4,982,843
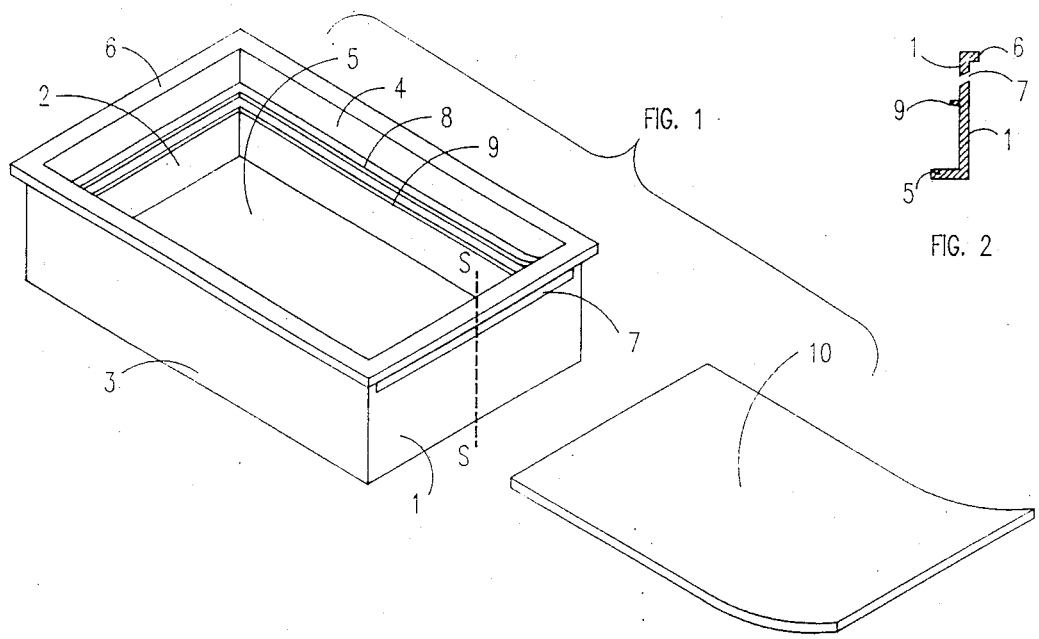
FIG. 1
FIG. 2
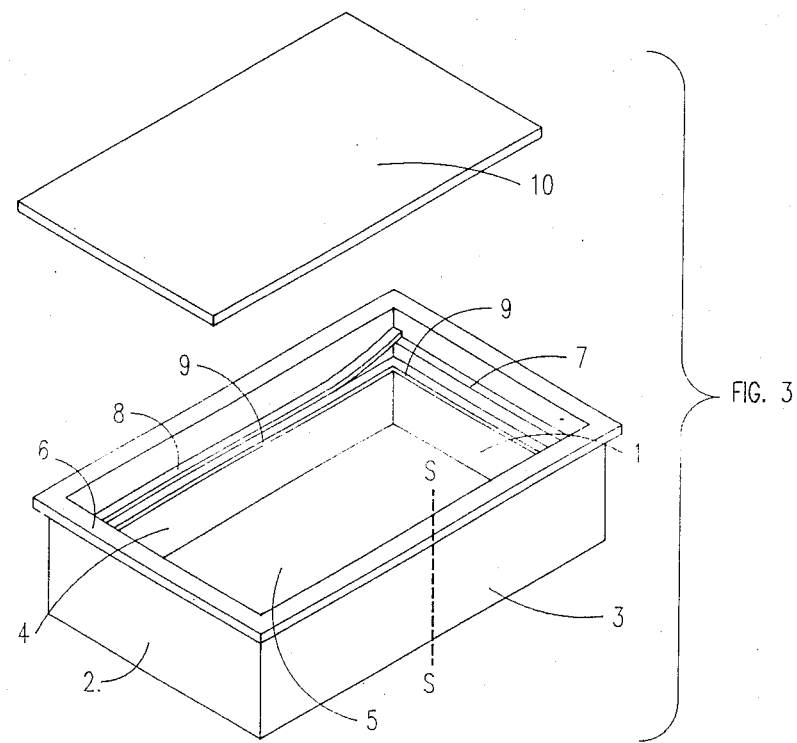
FIG. 3
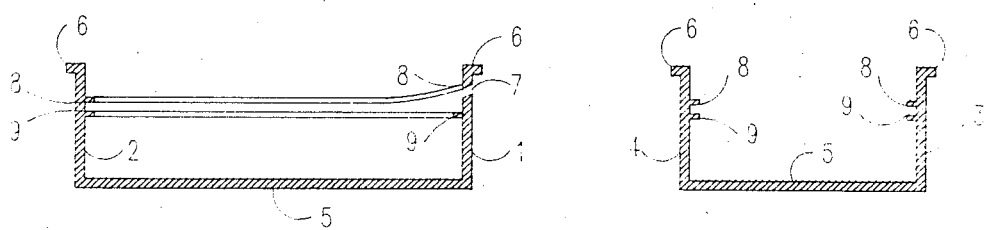
FIG. 4
FIG. 5

SHARPS DISPOSAL UNIT

BACKGROUND OF THE INVENTION

1. Field of the Invention

The invention relates generally to a single-use disposal unit for sharp objects, like needles and syringes, that could pose a threat because of their potential for injury and infection.

2. Description or the Prior Art

Sharp objects, like needles and syringes, that are used in hospitals, clinics, or doctor's offices, are at present discarded in plastic sharps containers which are multiple use and open to the air. They are constructed in such a way that the sharp objects can be pushed in, but not retrieved again without injury. When the container is full, it is capped and disposed of according to protocol.

Although the containers are kept within easy reach of work areas, staff still has to walk to them, carrying the used and contaminated sharps for disposal. This increases the risks and is not desirable. Having to push the sharp objects into the container poses a potential for injury in itself. Since the same container is in use until it is full, which can take several days, potentially infectious objects are left open to contaminate the environment. With new and virulent infectious agents around, like HIV, this is a dangerous practice.

This invention offers a quick and safe method of disposal for sharps that eliminates the risks of the present method.

SUMMARY OF THE INVENTION

The invention relates to a box of rigid plastic with a separate, flexible lid that can close the box by sliding it through a slot in one side of the box. When the sharp objects are discarded into the box, the lid is pushed all the way in and will drop onto a rim below the slot that will effectively prevent it from being pushed out again. The box will be permanently locked, forming a disposal unit. The box can also be used as a supply unit, in which case the slot can be sealed with a paper strip from the inside and the top sealed with a paper cover, securing the contents in a sterile condition. After use, the supply unit becomes it's own disposal unit.

It is an object of the invention to provide a small, easy to use, absolutely safe, single-use disposal unit for anything sharp or infected that can be stored or carried around anywhere and that will help to eliminate needle-stick injuries.

It is another object of the invention to provide a device that can double as a supply and disposal unit, making it especially valuable for in-home care.

BRIEF DESCRIPTION OF THE DRAWINGS

FIG. 1 is an elevational view of an open disposal box, showing a slot in the front end and tracks for the insertion of a lid. The separate lid is shown in a slightly flexed position.

FIG. 2 is a sectional view of FIG. 1 along the line S————S, showing the downward sloping slot and the projecting rim of the lower track.

FIG. 3 is a different aspect of FIG. 1, showing more clearly the details of the sliding track for the lid.

FIG. 4 is a sectional view of one side of the box, showing the downward slope of the slot and corresponding shape of the sliding track.

FIG. 5 is a sectional view of FIG. 3 along the line S————S, showing the projections of the sliding track.

DESCRIPTION OF THE PREFERRED EMBODIMENT

Referring to FIG. 1, an embodiment of the invention is shown. An open box of rigid plastic shows a slot 7 in it's front end 1, the slot 7 being situated close to the top of the box and extending across it's entire width. The inner aspects of the side 4, back 2 and opposite side 3 of the box bear a sliding track composed of an upper rim 8 and a lower rim 9. A flat lid 10 is provided, made of a firm, but flexible plastic, that fits through the slot 7 in the front end 1 of the disposal box. When the lid 10 is pushed through the slot 7, it will slide between the upper rim 8 and the lower rim 9 of the sliding track until it is all the way pushed in to close the box. To facilitate the last push that will make the lid 10 engage the sliding track at the back 2 of the box, the lid 10 could be provided with an indentation for pushing with a thumb. The disposal box also shows a rim 6 around the top. This is provided to receive a paper closure when the box is used as a supply unit, to seal in the contents and keep them in a sterile condition. The slot 7 would then be sealed from the inside with a paper strip.

Referring to FIG. 2, a cross section of the front end 1 of the disposal box is shown. Here it is seen that the slot 7 through which the lid 10 will be pushed has a downward slope to facilitate the sliding of the lid 10. The lower rim 9 of the sliding track continues around the inner aspect of the front end 1 of the box just below the slot 7, forming a step, as best seen in FIG. 2, on which the lid 10 will come to rest when it is pushed in all the way. It is now impossible to slide the lid out again, as there is no way to lift it back up to the slot.

Referring to FIG. 3, another aspect of the invention is shown. The upper rim 8 of the sliding track curves gently upwards as it meets the upper edge of the slot 7, providing a guide for the sliding lid 10. The continuation of the lower rim 9 of the sliding track is shown just below the slot 7.

Referring to FIG. 4, a cross section of one side of the box is shown. Here can be seen more clearly the upward curve of the upper rim 8 of the sliding track and how it meets the slot 7, thus providing a continuation to the slope of slot 7 as a smooth guide for the sliding lid 10.

Referring to FIG. 5, a sectional view of FIG. 3 is shown, along the line S————S. It shows the protrusions of the upper rim 8 and the lower rim 9 of the sliding track that will hold the lid 10 in place after insertion.

Although an embodiment of the invention is illustrated in the drawings and previously described in detail, this invention encompasses any design and relationship of components which will function in a similar manner and which will provide the equivalent results.

I claim:

1. A sharps disposal unit comprising:
   (a) a box made of rigid plastic, having a bottom, a front, a back and two sides, defining an open top;
   (b) an unattached, flat lid of a firm, but flexible plastic, of a shape to complement the open top;
   (c) a slot in the front of the box, across it's width and close to it's upper edge, to receive the lid and showing a downward slope to facilitate the sliding in of the lid;

(d) tracks along the inner aspect of the sides and back of the box, close to the top, composed of an upper rim and a lower rim, with a space in between for the lid to slide in, the upper rim running parallel to the lower rim along the back of the box, continuing parallel on both sides along the sides of the box until it approaches the front, when the upper rim curves upwards and away from the lower rim to meet either end of the upper edge of the slot in the front of the box and the lower rim running parallel to the upper rim along the back and most of the sides of the box, but continues in a straight line when the upper rim begins to curve upwards, then continues in a straight line along the inner front of the box, forming a step below the slot.

2. A sharps disposal unit as recited in claim 1 in which the lid can be pushed through the slot in the front of the box and will slide inside the tracks on both sides until it engages the tracks at the back of the box, when the front of the lid will fall on the step below the slot which will effectively prevent it from being pushed out again and there being no means of lifting the lid, will thus lock the box permanently.

* * * * *